United States Patent
Levin et al.

[11] Patent Number: 5,977,408
[45] Date of Patent: *Nov. 2, 1999

[54] PREPARATION AND USE OF β-SULFONAMIDO HYDROXAMIC ACIDS AS MATRIX METALLOPROTEINASE AND TACE INHIBITORS

[75] Inventors: Jeremy Ian Levin, Nanuet; Arie Zask, New York; Yansong Gu, Pearl River, all of N.Y.

[73] Assignee: American Cyanamid Company, Madison, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/944,189

[22] Filed: Oct. 6, 1997

Related U.S. Application Data

[60] Provisional application No. 60/028,503, Oct. 16, 1996.
[51] Int. Cl.⁶ .................................................. C07C 311/29
[52] U.S. Cl. ............................................ 562/622; 562/621
[58] Field of Search ...................................... 562/622, 621

[56] References Cited

U.S. PATENT DOCUMENTS

| | | |
|---|---|---|
| 5,455,258 | 10/1995 | MacPherson et al. . |
| 5,506,242 | 4/1996 | MacPherson et al. . |
| 5,552,419 | 9/1996 | MacPherson et al. . |

FOREIGN PATENT DOCUMENTS

| | | |
|---|---|---|
| 606046 | of 0000 | European Pat. Off. . |
| 757984 | of 0000 | European Pat. Off. . |
| 780386 | of 0000 | European Pat. Off. . |
| WO 9535276 | of 0000 | WIPO . |
| WO9535275 | of 0000 | WIPO . |
| WO9600214 | of 0000 | WIPO . |
| WO9633172 | of 0000 | WIPO . |
| WO9718194 | of 0000 | WIPO . |
| WO9720824 | of 0000 | WIPO . |
| WO9722587 | of 0000 | WIPO . |
| WO9724117 | of 0000 | WIPO . |
| WO9727174 | of 0000 | WIPO . |
| WO 96/27583 | 9/1996 | WIPO .............................. C07C 311/29 |
| WO9719068 | 5/1997 | WIPO .......................... C07D 295/08 |

OTHER PUBLICATIONS

J. Med. Chem., 40, 2525, MacPherson et al. (1997).

Primary Examiner—Gary Geist
Assistant Examiner—Brian J. Davis
Attorney, Agent, or Firm—Rebecca R. Barrett

[57] ABSTRACT

The present invention relates to the discovery of novel, low molecular weight, non-peptide inhibitors of matrix metalloproteinases (e.g. gelatinases, stromelysins and collagenases) and TNF-α converting enzyme (TACE, tumor necrosis factor-α converting enzyme) which are useful for the treatment of diseases in which these enzymes are implicated such as arthritis, tumor growth and metastasis, angiogenesis, tissue ulceration, abnormal wound healing, periodontal disease, bone disease, proteinuria, aneurysmal aortic disease, degenerative cartilage loss following traumatic joint injury, demyelinating diseases of the nervous system, graft rejection, cachexia, anorexia, inflammation, fever, insulin resistance, septic shock, congestive heart failure, inflammatory disease of the central nervous system, inflammatory bowel disease, HIV infection, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization.

The TACE and MMP inhibiting ortho-sulfonamido aryl hydroxamic acids of the present invention are represented by the formula

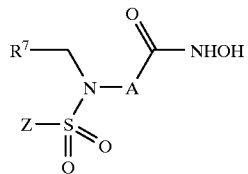

where the hydroxamic acid moiety and the sulfonamido moiety are bonded to adjacent carbons on group A where:

A is a 5 to 7 membered, monocyclic, non-aromatic heterocyclic ring having from 1 to 2 heteroatoms independently selected from N, O, and S, optionally substituted by $R^1$, $R^2$, $R^3$ and $R^4$;

a —$C_3$–$C_7$-cycloalkyl containing 0–2 double bonds and optionally substituted with $R^1$, $R^2$, $R^3$ and $R^4$;

or —$CHR^5$=$CHR^6$—;

and Z, $R^1$, $R^2$, $R^3$, $R^4$, $R^5$, $R^6$, $R^7$, $R^8$ and $R^9$ are described in the specification, and the pharmaceutically acceptable salts thereof, and the optical isomers and diastereomers thereof.

9 Claims, No Drawings

PREPARATION AND USE OF β-SULFONAMIDO HYDROXAMIC ACIDS AS MATRIX METALLOPROTEINASE AND TACE INHIBITORS

This application claims the benefit of prior U.S. Provisional application No. 60/028,503 filed Oct. 16, 1996.

BACKGROUND OF THE INVENTION

The present invention relates to the discovery of novel, low molecular weight, non-peptide inhibitors of matrix metalloproteinases (e.g. gelatinases, stromelysins and collagenases) and TNF-α converting enzyme (TACE, tumor necrosis factor-α converting enzyme) which are useful for the treatment of diseases in which these enzymes are implicated such as arthritis, tumor metastasis, tissue ulceration, abnormal wound healing, periodontal disease, bone disease, proteinuria, aneurysmal aortic disease, degenerative cartilage loss following traumatic joint injury, demyelinating diseases of the nervous system and HIV infection.

Matrix metalloproteinases (MMPs) are a group of enzymes that have been implicated in the pathological destruction of connective tissue and basement membranes [Woessner, J. F., Jr. FASEB J. 1991, 5, 2145; Birkedal-Hansen, H.; Moore, W. G. I.; Bodden, M. K.; Windsor, L. J.; Birkedal-Hansen, B.; DeCarlo, A.; Engler, J. A. *Crit. Rev. Oral Biol. Med.* 1993, 4, 197; Cawston, T. E. *Pharmacol. Ther.* 1996, 70, 163; Powell, W. C.; Matrisian, L. M. *Cur. Top. Microbiol. and Immunol.* 1996, 213, 1]. These zinc containing endopeptidases consist of several subsets of enzymes including collagenases, stromelysins and gelatinases. Of these classes, the gelatinases have been shown to be the MMPs most intimately involved with the growth and spread of tumors, while the collagenases have been associated with the pathogenesis of osteoarthritis [Howell, D. S.; Pelletier, J. -P. In *Arthritis and Allied Conditions*; McCarthy, D. J.; Koopman, W. J., Eds.; Lea and Febiger: Philadelphia, 1993; 12th Edition Vol. 2, pp. 1723; Dean, D. D. *Sem. Arthritis Rheum.* 1991, 20, 2; Crawford, H. C; Matrisian, L. M. *Invasion Metast.* 1994–95, 14, 234; Ray, J. M.; Stetler-Stevenson, W. G. *Exp. Opin. Invest. Drugs,* 1996, 5, 323].

It is known that the level of expression of gelatinase is elevated in malignancies, and that gelatinase can degrade the basement membrane which may lead to tumor metastasis [Powell, W. C.; Matisian, L. M. *Cur. Top. Microbiol. and Immunol.* 1996, 213, 1; Crawford, H. C; Matrisian, L. M. *Invasion Metast.* 1994–95, 14, 234; Ray, J. M.; Stetler-Stevenson, W. G. *Exp. Opin. Invest. Drugs,* 1996, 5, 323; Himelstein, B. P.; Canete-Soler, R.; Bernhard, E. J.; Dilks, D. W.; Muschel, R. J. *Invasion Metast.* 1994–95, 14, 246; Nuovo, G. J.; MacConnell, P. B.; Simsir, A.; Valea, F.; French, D. L. *Cancer Res.* 1995,55, 267–275; Walther, M. M.; Levy, A.; Hurley, K.; Venzon, D.; Linehen, W. M.; Steder-Stevenson, W. *J. Urol.* 1995, 153 (*Suppl.* 4), 403A; Tokuraku, M; Sato, H.; Murakarni, S.; Okada, Y.; Watanabe, Y.; Seiki, M. *Int. J. Cancer,* 1995, 64, 355; Himelstein, B.; Hua, J.; Bernhard, E.; Muschel, R. J. *Proc. Am. Assoc. Cancer Res. Ann. Meet.* 1996, 37, 632; Ueda, Y.; Imai, K.; Tsuchiya, H.; Fujimoto, N.; Nakanishi, I.; Katsuda, S.; Seiki, M.; Okada, Y. *Am. J. Pathol.* 1996, 148, 611; Gress, T. M.; Mueller-Pillasch, F.; Lerch, M. M.; Friess, H.; Buechler, M.; Adler, G. *Int. J. Cancer,* 1995, 62, 407; Kawashima, A.; Nakanishi, I.; Tsuchiya, H.; Roessner, A.; Obata, K.; Okada, Y. *Virchows Arch.,* 1994, 424, 547–552.]. Angiogenesis, required for the growth of solid tumors, has also recently been shown to have a gelatinase component to its pathology [Crawford, H. C; Matrisian, L. M. *Invasion Metast.* 1994–95,14, 234; Ray, J. M.; Steder-Stevenson, W. G. *Exp. Opin. Invest. Drugs,* 1996, 5, 323.]. Furthermore, there is evidence to suggest that gelatinase is involved in plaque rupture associated with atherosclerosis [Dollery, C. M.; McEwan, J. R.; Henney, A. M. *Circ. Res.* 1995, 77, 863; Zempo, N.; Koyama, N.; Kenagy, R. D.; Lea, H. J.; Clowes, A. W. *Arterioscler. Thromb. Vasc. Biol.* 1996,16, 28; Lee, R. T.; Schoen, F. J.; Loree, H. M.; Lark, M. W., Libby, P. *Arterioscler. Thromb. Vasc. Biol.* 1996, 16, 1070.]. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

The hypothesis that MMPs are important mediators of the tissue destruction that occurs in arthritis has long been considered, since it was first recognized that these enzymes are capable of degrading collagens and proteoglycans which are the major structural components of cartilage [Sapolsky, A. I.; Keiser, H.; Howell, D. S.; Woessner, J. F., Jr.; *J. Clin. Invest.* 1976, 58, 1030; Pelletier, J. -P.; Martel-Pelletier, J.; Howell, D. S.; Ghandur-Mnaymneh, L.; Enis, J. E.; Woessner, J. F., Jr., *Arthritis Rheum.* 1983, 26, 63.], and continues to develop as new MMPs are identified. For example, collagenase-3 (MMP-13) was cloned from breast cancer cells in 1994, and the first report that it could be involved in arthritis appeared in 1995 [Freiji, J. M.; Diez-Itza, I.; Balbin, M.; Sanchez, L. M.; Blasco, R.; Tolivia, J.; Lopez-Otin, C. *J. Biol. Chem.* 1994, 269, 16766; Flannery, C. R.; Sandy, J. D. 102–17, 41st *Ann. Meet. Orth. Res. Soc.* Orlando, Fla. Feb. 13–16, 1995.]. Evidence is accumulating that implicates MMP-13 in the pathogenesis of arthritis. A major structural component of articular cartilage, type II collagen, is the preferred substrate for MMP-13 and this enzyme is significantly more efficient at cleaving typeII collagen than the other collagenases [Knauper, V.; Lopez-Otin, C.; Smith, B.; Knight, G.; Murphy, G. *J. Biol. Chem.,* 1996, 271, 1544–1550; Mitchell, P. G.; Magna, H. A.; Reeves, L. M.; Lopresti-Morrow, L. L.; Yocum, S. A.; Rosner, P. J.; Geoghegan, K. F.; Hambor, J. E. *J. Clin. Invest.* 1996, 97, 761.]. MMP-13 is produced by chondrocytes, and elevated levels of MMP-13 has been found in human osteoartiritic tissues [Reboul, P.; Pelletier, J-P.; Hambor, J.; Magna, H.; Tardif, G.; Cloutier, J-M.; Martel-Pelletier, *J. Arthritis Rheum.* 1995,38 (*Suppl.* 9), S268;Shlopov, B. V.; Mainardi, C. L.; Hasty, K. A. *Arthritis Rheum.* 1995, 38 (*Suppl.* 9), S313; Reboul, P.; Pelletier, J-P.; Tardif, G.; Cloutier, J-M.; Martel-Pelletier, J. *J. Clin. Invest.* 1996, 97, 2011]. Potent inhibitors of MMPs were described over 10 years ago, but the poor bioavailability of these early peptidic, substrate mimetic MMP inhibitors precluded their evaluation in animal models of arthritis. More bioavailable, non-peptidic MMP inhibitors may be preferred for the treatment of diseases mediated by MMPs.

TNF-α converting enzyme catalyzes the formation of TNF-α from membrane bound TNF-α precursor protein. TNF-α is a pro-inflammatory cytokine that is now thought to have a role in rheumatoid arthritis, septic shock, graft rejection, insulin resistance and HIV infection in addition to its well documented antitumor properties. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.;

Isenberg, D. A.; Panayi, G. S. *Br. J. Rheumatol.* 1995, 34, 334; *Pharmaprojects,* 1996, Therapeutic Updates 17 (October), au197-M2Z.]. This observation has recently been extended to humans as well. Other conditions mediated by TNF-α are congestive heart failure, cachexia, anorexia, inflammation, fever, inflammatory disease of the central nervous system, and inflammatory bowel disease.

It is expected that small molecule inhibitors of gelatinase and TACE therefore have the potential for treating a variety of disease states. While a variety of MMP and TACE inhibitors have been identified and disclosed in the literature, the vast majority of these molecules are peptidic or peptide-like compounds that may have bioavailability and pharmacokinetic problems that would limit their clinical effectiveness. Low molecular weight, potent, long-acting, orally bioavailable inhibitors of gelatinases, collagenases and/or TACE are therefore highly desirable for the potential chronic treatment of the above mentioned disease states. Several non-peptidc, sulfur-containing hydroxamic acids have recently been disclosed and are listed below.

U.S. Pat. Nos. 5,455,258, 5,506,242 and 5,552,419, as well as European patent application EP606,046A1 and WIPO international publications WO96/00214 and WO97/22587 disclose non-peptide matrix metalloproteinase inhibitors of which the compound CGS27023A is representative. The discovery of this type of MMP inhibitor is further detailed by MacPherson, et. al. in *J. Med. Chem.*, (1997),40, 2525. Additional publications disclosing sulfonamide based MMP inhibitors which are variants of the sulfonamide-hydroxamate shown below, or the analogous sulfonamide-carboxylates, are European patent application EP-757984-Al and WIPO international publications WO95/35275, WO95/35276, WO96/27583, WO97/19068 and WO97/27174.

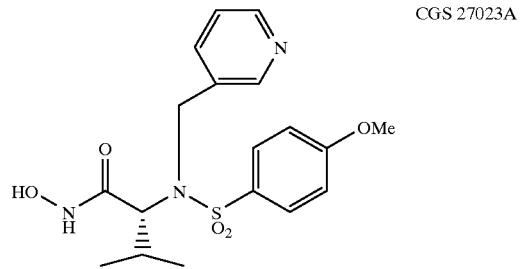

CGS 27023A

Publications disclosing β-sulfonamide-hydroxamate MMP inhibitor analogs of CGS 27023A in which the carbon alpha to the hydroxamic acid has been joined in a ring to the sulfonamide nitrogen, as shown below, include WIPO international publications WO96/33172 and WO97/20824.

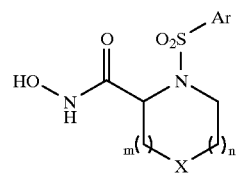

The German patent application DE19,542,189-A1 discloses additional examples of cylic sulfonamides as MMP inhibitors. In this case the sulfonamide-containing ring is fused to a phenyl ring to form an isoquinoline.

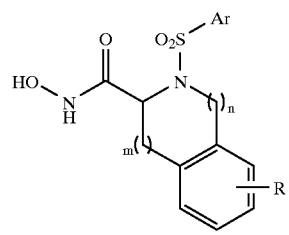

Analogs of the sulfonamide-hydroxamate MMP inhibitors in which the sulfonamide nitrogen has been replaced by a carbon atom, as shown in the general structure below, are European patent application EP-780386-A1 and WIPO international publication WO97/241 17.

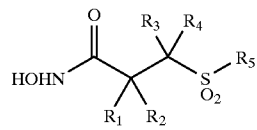

SUMMARY OF THE INVENTION

The TACE and MMP inhibiting β-sulfonamido hydroxamic acids of the present invention are represented by the formula

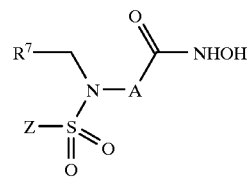

where the hydroxamic acid moiety and the sulfonamido moiety are bonded to adjacent carbons of group A where:

A is a 5 to 7 membered saturated or unsaturated monocyclic heterocyclic ring having from 1 to 2 heteroatoms independently selected from N, O, and S, optionally substituted by $R^1$, $R^2$, $R^3$ and $R^4$;

a $—C_3–C_7$-cycloalkyl containing 0–2 double bonds and optionally substituted with $R^1$, $R^2$, $R^3$ and $R^4$;

or $—CHR^5=CHR^6—$;

Z is aryl, heteroaryl, or heteroaryl fused to a phenyl, where aryl is phenyl or naphthyl optionally substituted by $R^1$, $R^2$, $R^3$ and $R^4$;

heteroaryl is a 5–6 membered heteroaromatic ring having from 1 to 3 heteroatoms independently selected from N, O, and S, and optionally substituted by $R^1$, $R^2$, $R^3$ and $R^4$;

and when heteroaryl is fused to phenyl, either or both of the rings can be optionally substituted by $R^1$, $R^2$, $R^3$ and $R^4$;

$R^1$, $R^2$, $R^3$ and $R^4$ are independently —H, —$OR^5$, —F,—Br, —Cl, —I, —$C(O)NR^5OR^6$, —CN, —OR5, —$C_1$–$C_4$-perfluoroalkyl, —$S(O)_xR^5$ where x is 0–2, —$OPO(OR^5)OR^6$, —$PO(OR_6)R_5$, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, —$NR^5C(=NR^6)NR^5R^6$, 3–6 membered cycloheteroalkyl having one to three heteroatoms independently selected from N, O, and S and optionally having 1 or 2 double bonds and optionally substituted by one to three groups each selected independently from $R^5$; -aryl or heteroaryl as defined above, —$SO_2NHCOR^5$ or —$CONHSO_2R^5$ where $R^5$ is not H; -tetrazol-5-yl, —$SO_2NHCN$, —$SO_2NHCONR^5R^6$ or straight chain or branched —$C_1$-$C_6$ alkyl, —$C_2$-$C_6$-alkenyl, or —$C_2$-$C_6$-alkynyl, or —$C_3$-$C_6$ cycloalkyl optionally having 1 or 2 double bonds each optionally substituted with —$COR^5$, —CN, —$C_2$-$C_6$ alkenyl, —$C_2$-$C_6$ alkynyl,—$OR^5$, —$C_1$-$C_4$-perfluoroalkyl, —$S(O)_xR^5$ where x is 0–2, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, —$C_3$-$C_6$ cycloalkyl as defined above, 3–6 membered cycloheteroalkyl as defined above, aryl or heteroaryl as defined above, —$SO_2NHCOR^5$ or—$CONHSO_2R^5$ where $R^5$ is not hydrogen, —$PO(OR^5)OR^6$, —$PO(OR^6)R^5$, -tetrazol-5-yl, —$C(O)NR^5OR^6$, —$NR^5C(=NR^6)NR^5R^6$, —$SO_2NHCONR^5R^6$ or —$SO_2NHCN$;

with the proviso that when $R^1$ and $R^2$ are on adjacent carbons of A, $R^1$ and $R^2$ together with the carbons to which they are attached can form a 5–7 membered saturated or unsaturated monocyclic heterocyclic ring, or a 5–6 membered heteroaryl ring, each having from 1 to 2 heteroatoms independently selected from N, O, and S, wherein said heterocyclic or heteroaryl ring may be optionally substituted by one to four groups each selected independently from $R^4$; or $R^1$ and $R^2$ together with the carbons to which they are attached can form a 5–7 membered saturated or unsaturated carbocyclic ring or an aryl ring wherein said carbocyclic or aryl ring may be optionally substituted by one to four groups each selected independently from $R^4$;

$R^5$ and $R^6$ are independently defined as H, aryl and heteroaryl as defined above, —$C_3$-$C_6$-cycloalkyl as defined above, —$C_3$-$C_6$-cycloheteroalkyl as defined above, —$C_1$-$C_4$-perfluoroalkyl, or straight chain or branched —$C_1$-$C_6$ alkyl, —$C_2$-$C_6$-alkenyl, or —$C_2$-$C_6$-alkynyl each optionally substituted with —OH, —$COR^8$, —CN, —$C(O)NR^8OR^9$, —$C_2$-$C_6$-alkenyl, —$C_2$-$C_6$-alkynyl, —$OR^8$, —$C_1$-$C_4$-perfluoroalkyl, —$S(O)_xR^8$ where x is 0–2, —$OPO(OR^8)OR^9$, —$PO(OR^8)R^9$, —$OC(O)NR^8R^9$, —$COOR^8$, ——$CONR^8R^9$, —$SO_3H$, —$NR^8R^9$,—$NCOR^8R^9$, —$NR^8COOR^9$, —$SO_2NR^8R^9$, —$NO_2$, —$N(R^8)SO_2R^9$, —$NR^8CONR^8R^9$, —$C_3$-$C_6$ cycloalkyl as defined above, —$C_3$-$C_6$-cycloheteroalkyl as defined above, -aryl or heteroaryl as defined above, —$SO_2NHCOR^8$ or —$CONHSO_2R^8$ where $R^8$ is not hyrdogen, -tetrazol-5-yl, —$NR^8C(=NR^9)NR^8R^9$, —$SO_2NHCONR^8R^9$, —$SO_2NHCN$;

$R^7$ is hydrogen, straight chain or branched —$C_1$-$C_6$-alkyl, —$C_2$-$C_6$-alkenyl, or —$C_2$-$C_6$-alkynyl each optionally substituted with —OH, —$COR^5$, —CN, —$C_2$-$C_6$-alkenyl, —$C_2$-$C_6$-alkynyl, —$OR^5$,—$C_1$-$C_4$-perfluoroalkyl, —$S(O)_xR^5$ where x is 0–2, —$OPO(OR^5)OR^6$, —$PO(OR^5)R^6$, —$OC(O)NR^5R^6$, —$COOR^5$, —$CONR^5R^6$, —$SO_3H$, —$NR^5R^6$,—$NR^5COR^6$, —$NR^5COOR^6$, $SO_2NR^5R^6$, —$NO_2$, —$N(R^5)SO_2R^6$, —$NR^5CONR^5R^6$, —$C_3$-$C_6$ cycloalkyl as defined above, —$C_3$-$C_6$-cycloheteroalkyl as defined above, -aryl or heteroaryl as defined above, —$SO_2NHCOR^5$ or —$CONHSO_2R^5$ where $R^5$ is not hydrogen, -tetrazol-5-yl, —$NR^5C(=NR6)NR^5R^6$, —$C(O)N R^5OR^6$, —$SO_2NHCONR^5R^6$ or —$SO_2NHCN$;

or $R^7$ is phenyl or naphthyl, optionally substituted by $R^1$, $R^2$, $R^3$ and $R^4$ or a 5 to 6 membered heteroaryl group having 1 to 3 heteroatoms selected independently from N, O, and S and optionally substituted by $R^1$, $R^2$, $R^3$ and $R^4$;

or $R^7$ is $C_3$-$C_6$ cycloalkyl or 3–6 membered cycloheteroalkyl as defined above;

or $R^7CH_2$—N—A—, where A is as defined above, can form with the carbon adjacent to the carbon bearing the sulfonamido group, a non-aromatic fused 7–10 membered heterocyclic ring optionally containing an additional heteroatomselected from O, S and N wherein said heterocyclic ring may be optionally fused to another benzene ring;

$R^8$ and $R^9$ are independently H, aryl or heteroaryl as defined above, —$C_3$-$C_7$-cycloalkyl or cycloheteroalkyl as defined above, —$C_1$-$C_4$-perfluoroalkyl, straight chain or branched —$C_1$-$C_6$-alkyl, —$C_2$-$C_6$-alkenyl, or —$C_2$-$C_6$-alkynyl, each optionally substituted with hydroxy, alkoxy, aryloxy, —$C_1$-$C_4$-perfluoroalkyl, amino, mono- and di-$C_1$-$C_6$-alkylamino, carboxylic acid, carboalkoxy and carboaryloxy, nitro, cyano, carboxamido primary, mono- and di-$C_1$-$C_6$-alkylcarbamoyl;

and the pharmaceutically acceptable salts thereof and the optical isomers and distereomers thereof.

The term "5–7 membered saturated or unsaturated monocyclic heterocyclic ring having from 1 to 2 heteroatoms independently selected from N, O, and S" as defined hereinabove includes, but is not limited to, tetrahydrofuran, tetrahydrothiophene, tetramethylene sulfone, tetrahydropyran, dihydropyran, pyrrolidine, morpholine and piperidine. The term "5 to 6 membered heteroaryl" as defined hereinabove includes, but is not limited to, pyrrole, furan, thiophene, pyridine, pyrimidine, pyridazine, pyrazine, triazole, pyrazole, imidazole, isothiazole, thiazole, isoxazole and oxazole. The term "heteroaryl fused to a phenyl" includes, but is not limited to, indole, isoindole, benzofuran, benzothiophene, quinoline, isoquinoline, quinoxaline, quinazoline, benzotriazole, indazole, benzimidazole, benzothiazole, benzisoxazole, and benzoxazole.

The following compounds (I–X) which may be used in preparing compounds of the invention are known and references are given hereinbelow.

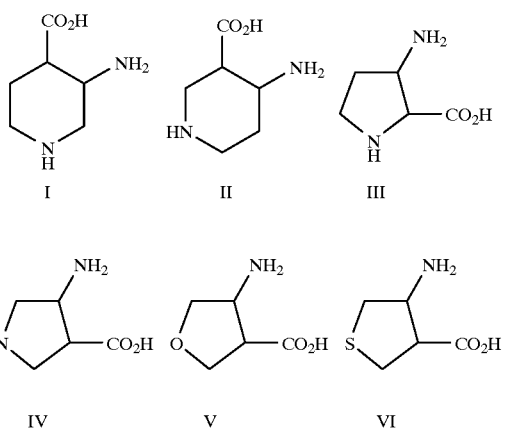

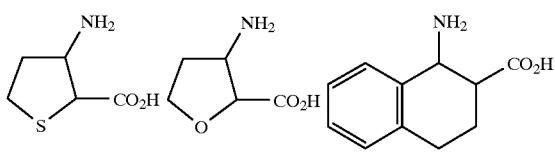

VII  VIII  IX

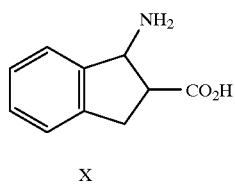

X

Compounds I and II:
Jacobsen, Poul; Schaumburg, Kjeld; Krogsgaard-Larsen, Povl. Acta Chem. Scand., Ser. B (1980), B34(5), 319–26.

Compound III:
a) Baldwin, Jack E.; Adlington, Robert M.; Gollins, David W.; Godfrey, Christopher R. A. Tetrahedron (1995), 51(17), 5169–80.
b) Gallina, C.; Marta, C.; Colombo, C.; Romeo, A. Tetrahedron (1971), 27(19), 4681–5.
c) Kogoori, Yasushi; Wakayama, Mikio; Sano, Tetsuya; Sato, Yuji. Jpn. Kokai Tokyo Koho, JP 04360866 A2.
d) Gallina, Carlo; Koch, Virginio; Romeo, Aurelio. Tetrahedron Lett. (1969), (35), 3055–6.

Compound IV:
a) Thorbek, Pia; Hjeds, Hans; Schaumburg, Kjeld. Acta Chem. Scand., Ser. B (1981), B35(7), 473–9.
b) Kunisch, Franz; Mittendorf, Joachim; Plempel, Manfred; Militzer, Hans Christian. Eur. Pat. Appl., EP 538692 A1.

Compound V:
a) Kunisch, Franz; Mittendorf, Joachim; Plempel, Manfred. Eur. Pat. Appl., EP 538688 A1.
b) Crowley, Patrick Jelf; Heaney, Stephen Paul; Lawson, Kevin Robert; Youle, David. PCT Int. Appl., WO 9507022 A1.

Compound VI:
a) Mittendorf, Joachim; Kunisch, Franz; Plempel, Manfred. Eur. Pat. Appl., EP 538691 A1.
b) Crowley, Patrick Jelf; Heaney, Stephen Paul; Lawson, Kevin Robert; Youle, David. PCT Int. Appl., WO 9507022 A1.

Compound VII:
Mittendorf, Joachim; Kunisch, Franz; Plempel, Manfred. Eur. Pat. Appl., EP 538691 A1.

Compound VIII:
Kunisch, Franz; Mittendorf, Joachim; Plempel, Manfred. Eur. Pat. Appl., EP 538688 A1.

Compound IX:
Malis, Jerry L.; Rosenthale, Marvin E. U.S. Pat. No. 3,746,495.

Compound X:
Ohki, Hidenori; Inamoto, Yoshiko; Kawabata, Kohji; Kamimura, Toshiaki; Sakane, Kazuo. J. Antibiot. (1991), 44(5), 546–9.

The compounds of this invention are shown to inhibit the enzymes MMP-1, MMP-9, MMP-13 and TNF-α converting enzyme (TACE) and are therefore useful in the treatment of arthritis, tumor metastasis, tissue ulceration, abnormal wound healing, periodontal disease, graft rejection, insulin resistance, bone disease and HIV infection.

DETAILED DESCRIPTION OF THE INVENTION

The following reaction scheme (Scheme I) shows the general reaction route followed for the synthesis of hydroxamic acids of this invention. For purposes of illustration only, trans-2-aminocyclohexane carboxylic acid, wherein A is represented by a cyclohexyl ring, is sulfonylated with p-methoxybenzene sulfonamide, wherein Z is p-methoxybenzene, to provide a sulfonamide which is first converted into its t-butyl ester and then alkylated with benzyl bromide, wherein $R^7$ is benzyl, to give the N,N-disubstituted sulfonamide which is subsequently converted into the corresponding hydroxamic acid in two steps.

Scheme I

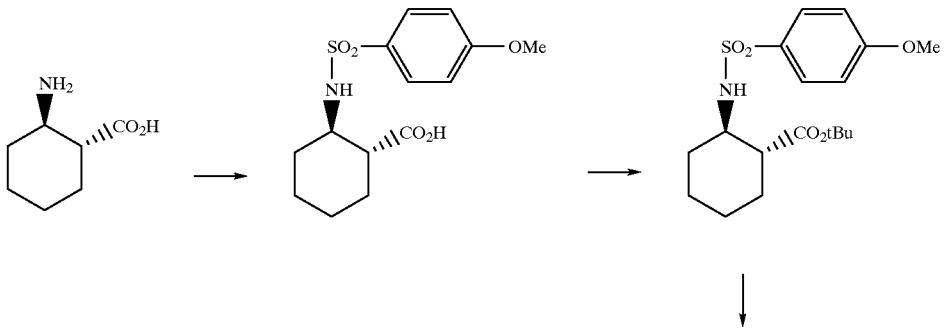

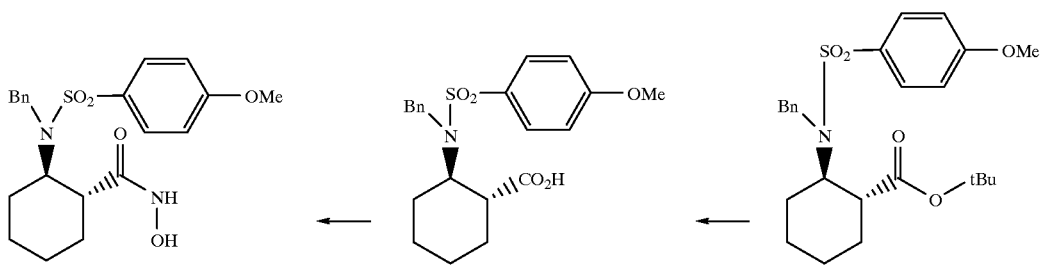

Schemes II and III illustrate two methods for incorporating amino groups into the substituent attached to the sulfonamide nitrogen of the compounds of the invention. Thus, in Scheme II the NH-sulfonamide is alkylated with propargyl bromide to provide the propargyl sulfonamide. This alkyne is reacted with paraformaldehyde in the presence of a primary or secondary amine and cuprous chloride to give the propargyl amine which is converted, as before, to the desired hydroxamic acid.

Scheme II

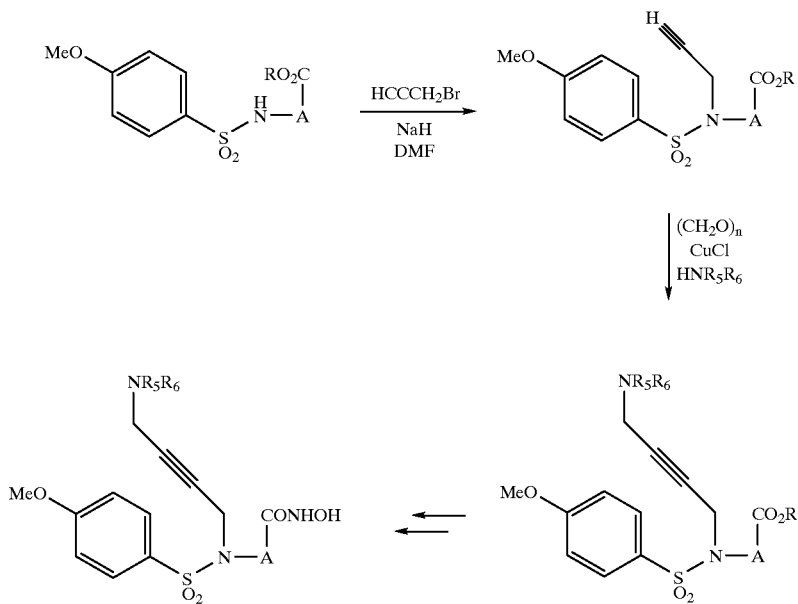

In Scheme III, selective hydrolysis of the ester of the p-carboethoxybenzyl sulfonamide group provides a monocarboxylic acid. This acid may be converted into an amide (not shown), followed by conversion of the ester A—$CO_2R$ into the corresponding hydroxamate, or reduced to the corresponding alcohol with diborane. The alcohol may be converted into the analogous amine via the benzylic bromide, followed by conversion of the ester A—$CO_2R$ into the corresponding hydroxamate.

Scheme III

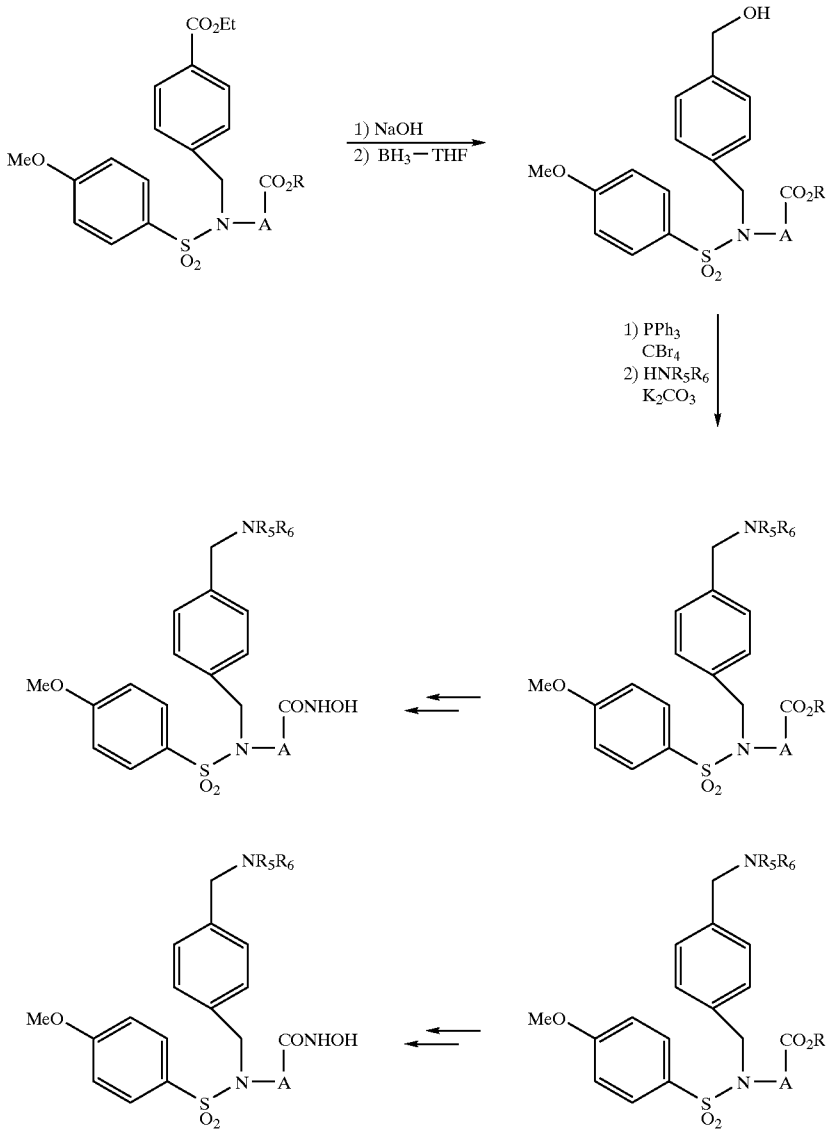

Methods for synthesizing variations of substituents on the sulfonyl aryl group are shown in Schemes IV through VI. As shown in Scheme IV, biaryl sulfonyl groups are synthesized by Suzuki couplings on a bromo-substituted benzene sulfonamide. The starting bromo-substituted benzene sulfonamide is synthesized from the commercially available bromobenzenesulfonyl chloride and the amino-acid or aminoester, $H_2N$—A—$CO_2R$, followed by alkylation of the resulting NH-sulfonamide. Alternatively, the bromo aryl sulfonamide is converted into the corresponding boronic acid by the method of Ishiyama, et.al. [J. Org. Chem. (1995), 60, 7508] followed by coupling with an appropriate aryl halide.

Scheme IV

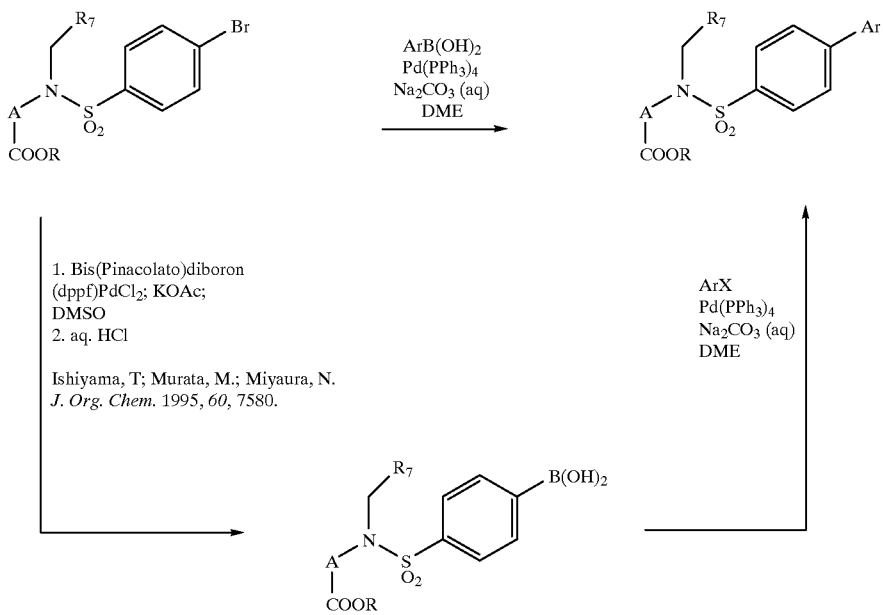

Methods for synthesizing sulfonyl aryl ethers are shown in Schemes V through VII. In Scheme V biaryl ethers, or aryl heteroaryl ethers, are synthesized starting from the known sulfonyl chlorides (see for example: Zook SE; Dagnino, R; Deason, ME, Bender, SL; Melnick, MJ WO 97/20824).

Scheme V

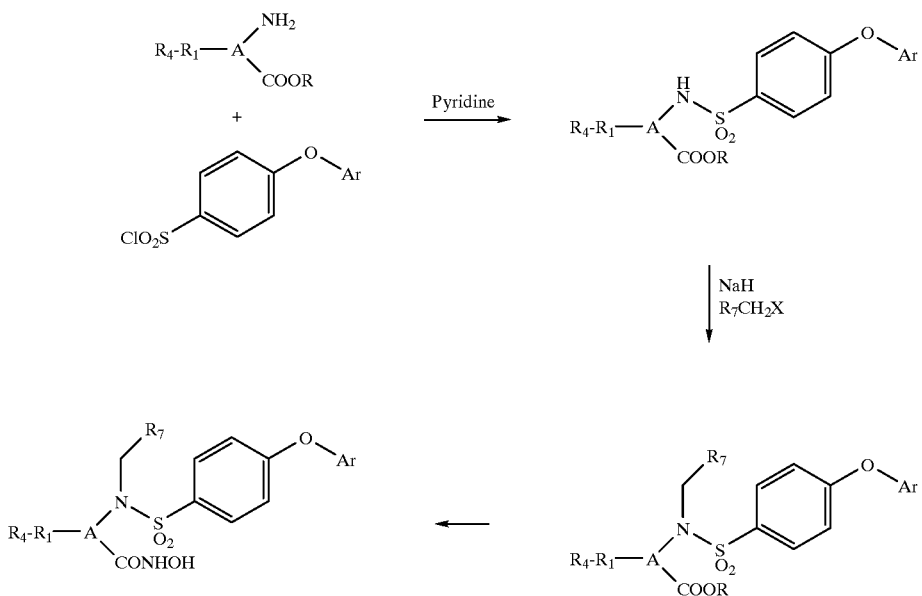

Alternatively, the biaryl ethers may be prepared from the corresponding boronic acids or via the sulfonyl phenols as shown in Scheme VI.

Scheme VI
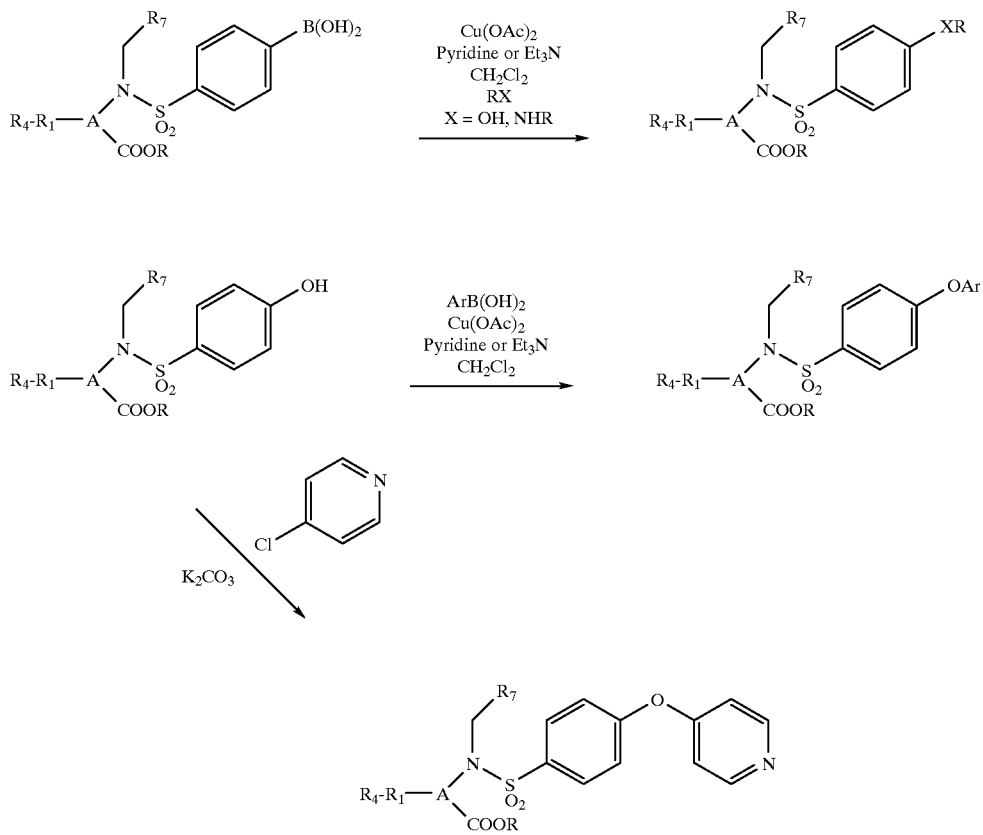
Aryl ethers may also be prepared via displacement of the fluorine from a parafluorobenzene sulfonamide, as shown in Scheme VII. Aryl or alkyl ethers may be prepared in this manner.
Scheme VII
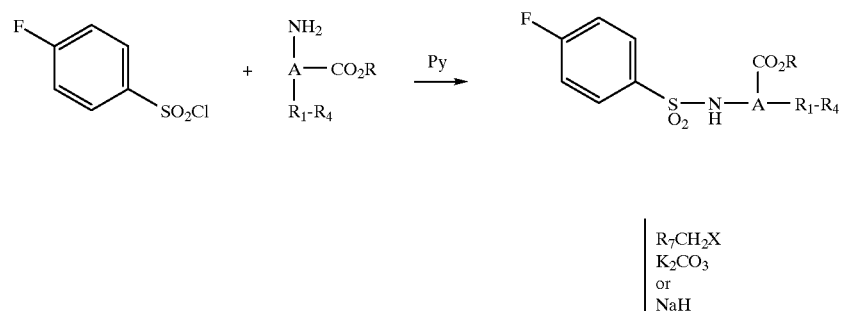

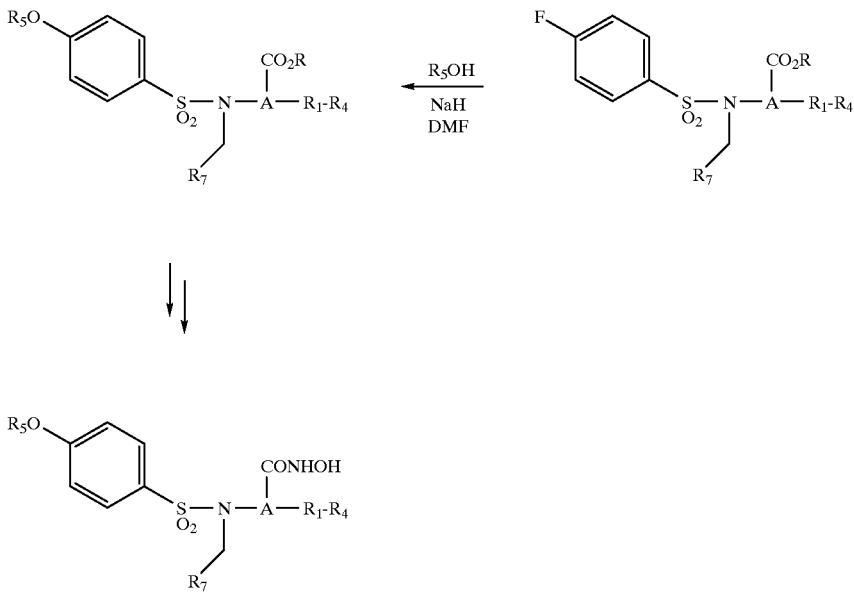

Starting materials for other groups, A, of the invention are synthetically accecssible. For example, the piperidine analogs shown in Scheme VIII should be readily available from the analogous pyridines via hydrogenation.

Scheme VIII

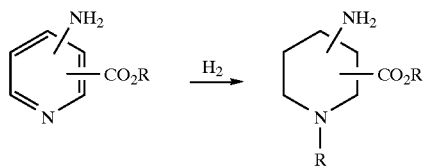

Basic salts of the hydroxamic acids can be formed with pharmaceutically acceptable alkali-forming metal cations such as lithium, sodium, potassium, calcium and aluminum. Acid addition salts can be formed when a substitutent contains a basic amino group using a pharmaceutically acceptable inorganic or organic acid such as hydrochloric, hydrobromic, phosphoric, sulfuric, acetic, benzoic, succinic, lactic, malic, maleic, fumaric or methanesulfonic acids.

The following specific examples are included for illustrative purposes and are not to be construed as limiting to this disclosure in any way. Other procedures useful for the preparation of compounds of this invention will be apparent to those skilled in the art.

EXAMPLE 1
(trans)-2-(4-Methoxybenzenesulfonyl)aminocyclohexane-carboxylic acid To a room temperature solution of 1 g (6.8 mmol) of trans-2-amino-1-cyclohexylcarboxylic acid in 50 ml of dioxane:$H_2O$ (1:1) containing 1.7 ml (12.2 mmol) of triethylamine was added 1.54 g (7.46 mmol) of 4-methoxybenzenesulfonyl chloride. The mixture was stirred at 25° C. for 18 h. The resulting mixture was diluted with pentane to afford 1.119 g (51%) of the desired sulfonamide product as a white solid. $^1$H NMR(DMSO-$d_6$): 7.7 ppm (dd, 2H, Ar), 7.4 ppm (d, 1H, NH), 7.0 ppm (dd, 2H, Ar), 3.8 ppm (s, 3H, OMe), 3.5 ppm (m, 1H, N—CH), 1.0–1.7 ppm (m, 9H, hydrocarbon).

EXAMPLE 2
(cis)-2-(4-Methoxybenzenesulfonyl)aminocyclohexane-carboxylic acid In the same manner as described in Example 1, 2.5 g (17 mmol) of cis-2-amino-1-cyclohexylcarboxylic acid provided 3.283 g (60%) of the desired carboxylic acid. Electrospray Mass Spec 314.1 (M+H).

EXAMPLE 3
(trans)-2-(4-Methoxybenzenesulfonyl)aminocyclohexane-carboxylic acid t-butyl ester To a solution of 0.313 g (1 mmol) of the product from Example 1 in 5.0 mL of toluene was added 1 mL (4 mmol) of N,N-dimethylformamide di-tert-butyl acetal. The resulting mixture was heated at 110° C. for 4 h under nitrogen and then allowed to cool to room temperature. The solution was then poured on top of a silica gel column. Chromatography on silica gel eluting with 10–20% ethyl acetate/hexane gave 353 mg (96%) of the desired ester as a white solid. $^1$H NMR(CDCl$_3$): 7.8 ppm (dd, 2H, Ar), 7.0 ppm (dd, 2H, Ar), 5.7 ppm (d, 1H, NH), 3.9 ppm (s, 3H, OMe), 3.4 ppm (m, 1H, N—CH), 2.5 ppm (m, 1H, CH—CO$_2$—), 1.0–2.0 ppm (m, 17H, hydrocarbon).

EXAMPLE 4
(cis)-2-(4-Methoxy-benzenesulfonylamino)-cyclohexane-carboxylic acid tert-butyl ester In the same manner as described in Example 3, 1.438 g (4.59 mmol) of the product from Example 2 provided 0.739 g (44%) of the desired tert-butyl ester as a colorless oil. Electrospray Mass Spec 370.1 (M+H).

EXAMPLE 5
(trans)-2-[Benzyl-(4-methoxybenzenesulfonyl)amino]-cyclohexanecarboxylic acid t-butyl ester To a solution of 1.146 g (3.1 mmol) of the product from Example 3 in 31 mL of DMF was added 0.137 g (3.42 mmol) of 60% sodium hydride. The resulting mixture was stirred for 30 min at 25° C. and then 0.42 mL (3.50 mmol) of benzyl bromide was added all at once. This reaction mixture was stirred for 10 hr at 55° C. and then poured into water and extracted with ether. The combined organics were washed with water and brine, dried over $MgSO_4$, filtered and concentrated in vacuo to provide a white solid which was recrystallized from EtOAc/Hexanes to provide 1.364 g (95%) of the desired product. $^1H$ NMR($CDCl_3$): 7.7 ppm (dd, 2H, Ar), 7.1–7.4 (m, 5H, Ar), 6.9 ppm (dd, 2H, Ar), 4.5–4.7 ppm (AB quartet, 2H, $CH_2$—A*r*), 3.9 ppm (s, 3H, OM*e*), 4.0 ppm (m, 1H, N—CH), 2.9 ppm (m, 1H, CH—$CO_2$—), 1.0–2.3 ppm (m, 17H, hydrocarbon protons).

EXAMPLE 6
(cis)-2-[Benzyl-(4-methoxy-benzenesulfonyl)-amino]-cyclohexanecarboxylic acid tert-butyl ester In the same manner as described in Example 5, 0.600 g (1.62 mmol) of the product from Example 4 provided 0.310 g (42%) of the desired benzylated ester as a colorless oil. Electrospray Mass Spec 460.1 (M+H).

EXAMPLE 7
(trans)-2-[Benzyl-(4-methoxy-benzenesulfonyl)-amino]-cyclohexanecarboxylic acid To a solution of 1.364 g (2.97 mmol) of the product from Example 5 in 10 mL of dichloromethane was added 10 mL of trifluoroacetic acid and the mixture was stirred for 4 h at room temperature. The solvent was then concentrated in vacuo and the residue was chromatographed on silica gel eluting with 10–100% ethyl acetate/hexane to provide 1.092 g (73%) of the desired product as a white solid. Electrospray Mass Spec 404.2 (M+H)

EXAMPLE 8
(cis)-2-[Benzyl-(4-methoxy-benzenesulfonyl)-amino]-cyclohexanecarboxylic acid In the same manner as described in Example 7, 0.240 g (0.522 mmol) of the product from Example 6 provided 0.207 g (98%) of the desired carboxylic acid as a white solid. Electrospray Mass Spec 404.0 (M–H).

EXAMPLE 9
(trans)-2-[Benzyl-(4-methoxy-benzenesulfonyl) -amino]-cyclohexanecarboxylic acid hydroxyamide To a solution of 807 mg (2 mmol) of the product from Example 7 in 20 mL of dichloromethane was added 0.05 mL of DMF followed by 2.2 mL (2.52 mmol) of a 2 M solution of oxalyl chloride and the resulting reaction mixture was stirred at room temperature for 0.5 h.

In a separate flask, 4 mL (29 mmol) of triethylamine was added to a 0° C. mixture of 695 mg (10 mmol) of hydroxylamine hydrochloride in 22 mL of THF and 5 mL of water. After this mixture had been stirred for 15 min at 0° C., the acid chloride solution was added to it in one portion and the resulting solution was allowed to warm to room temperature and stirred for another 4 h. Water was then added to the reaction flask and 854 mg (100% yield) of the desired hydroxamic acid was collected via filtration as a white solid. Electrospray Mass Spec 419.3 (M+H)

EXAMPLE 10
(cis)-2-[Benzyl-(4-methoxy-benzenesulfonyl)-amino]-cyclohexanecarboxylic acid hydroxyamide In the same manner as described in Example 9, 0.144 g (0.357 mmol) of the product from Example 8 provided 0.90 g (60%) of the desired carboxylic acid as a white solid. Electrospray Mass Spec 419.1 (M+H).

Pharmacology

Procedures for Measuring MMP-1, MMP-9, and MMP-13 Inhibition

These assays are based on the cleavage of a thiopeptide substrates such as Ac-Pro-Leu-Gly(2-mercapto-4methyl-pentanoyl)-Leu-Gly-OEt by the matrix metalloproteinases MMP-1, MMP-13 (collagenases) or MMP-9 (gelatinase), which results in the release of a substrate product that reacts colorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with assay buffer (50 mM HEPES, pH 7.5, 5 mM $CaCl_2$, 0.02% Brij) to the desired final concentration. The assay buffer, enzyme, vehicle or inhibitor, and DTNB/substrate are added in this order to a 96 well plate (total reaction volume of 200 μl) and the increase in color is monitored spectrophotometrically for 5 minutes at 405 nm on a plate reader and the increase in color over time is plotted as a linear line.

Alternatively, a fluorescent peptide substrate is used. In this assay, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM $Ca^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide assays, the slope of the line is calculated and represents the reaction rate. The linearity of the reaction rate is confirmed ($r^2 > 0.85$). The mean (x±sem) of the control rate is calculated and compared for statistical significance ($p < 0.05$) with drug-treated rates using Dunnett's multiple comparison test. Dose-response relationships can be generated using multiple doses of drug and $IC_{50}$ values with 95% CI are estimated using linear regression.

Procedure for Measuring TACE Inhibition

Using 96-well black microtiter plates, each well receives a solution composed of 10 μL TACE (Immunex, final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2>0.85$). The mean (x±sem) of the control rate is calculated and compared for statistical significance ($p<0.05$) with drug-treated rates using Dunnett's multiple comparison test. Dose-response relationships can be generate using multiple doses of drug and $IC_{50}$ values with 95% CI are estimated using linear regression.

Results of the above in-vitro matrix metalloproteinase inhibition and TACE inhibition pharmacological assays are given in Table I below.

TABLE I

| | Inhibition of MMP and TACE | | | |
|---|---|---|---|---|
| Example | MMP-1[1] | MMP-9[1] | MMP-13[1] | TACE[1] |
| 9 | 176 | 181 | 233 | 1612 |
| 10 | 616 | 275 | 286 | 24% |

[1]$IC_{50}$ nM or % inhibition at 1 μM concentration

Pharmaceutical Composition

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP or TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed:
1. A compound having the formula:

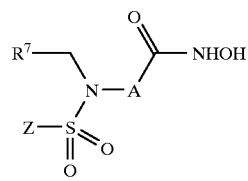

where the hydroxamic acid moiety and the sulfonamido moiety are bonded to adjacent carbons of group A where:
A is a 5 to 7 membered, monocyclic, non-aromatic heterocyclic ring having from 1 to 2 heteroatoms independently selected from N, O, and S, optionally substituted by $R^1$, $R^2$, $R^3$ and $R^4$;
a —$C_3$–$C_7$-cycloalkyl containing 0–2 double bonds and optionally substituted with $R^1$, $R^2$, $R^3$ and $R^4$;
or —$CHR^5$=$CHR^6$—;
Z is aryl, heteroaryl, or heteroaryl fused to a phenyl, where aryl is phenyl or naphthyl optionally substituted by $R^1$, $R^2$, $R^3$ and $R^4$;

heteroaryl is a 5–6 membered heteroaromatic ring having from 1 to 3 heteroatoms independently selected from N, O, and S, and optionally substituted by $R^1$, $R^2$, $R^3$ and $R^4$;

and when heteroaryl is fused to phenyl, either or both of the rings can be optionally substituted by $R^1$, $R^2$, $R^3$ and $R^4$;

$R^1$, $R^2$, $R^3$ and $R^4$ are independently —H, —COR$^5$, —F, —Br, —Cl, —I, —C(O)NR$^5$OR$^6$, —CN, —OR$^5$, —C$_1$-C$_4$-perfluoroalkyl, —S(O)$_x$R$^5$ where x is 0–2, —OPO(OR$^5$)OR$^6$, —PO(OR$_6$)R$_5$, —OC(O)NR$^5$R$^6$, —COOR$^5$, —CONR$^5$R$^6$, —SO$_3$H, —NR$^5$R$^6$, —NR$^5$COR$^6$, —NR$^5$COOR$^6$, —SO$_2$NR$^5$R$^6$, —NO$_2$, —N(R$^5$)SO$_2$R$^6$, —NR$^5$CONR$^5$R$^6$, —NR$^5$C(=NR$^6$)NR$^5$R$^6$, —C$_3$-C$_6$-cycloalkyl optionally having 1 or 2 double bonds and optionally substituted with one to three groups each selected independently from R$^5$, 3–6 membered cycloheteroalkyl having one to four heteroatoms independently selected from N, O, and S, optionally having 1 or 2 double bonds and optionally substituted by one to three groups each selected independently from R$^5$; -aryl or heteroaryl as defined above, —SO$_2$NHCOR$^5$ or —CONHSO$_2$R$^5$ where R$^5$ is not H, -tetrazol-5-yl, —SO$_2$NHCN, —SO$_2$NHCONR$^5$R$^6$ or straight chain or branched —C$_1$-C$_6$ alkyl, —C$_2$-C$_6$-alkenyl, or —C$_2$-C$_6$-alkynyl each optionally substituted with —COR$^5$, —CN, —C$_2$-C$_6$ alkenyl, —C$_2$-C$_6$ alkynyl, —OR$^5$, —C$_1$-C$_4$-perfluoroalkyl, —S(O)$_x$R$^5$ where x is 0–2, —OC(O)NR$^5$R$^6$, —COOR$^5$, —CONR$^5$R$^6$, —SO$_3$H, —NR$^5$R$^6$, —NR$^5$COR$^6$, —NR$^5$COOR$^6$, —SO$_2$NR$^5$R$^6$, —NO$_2$, —N(R$^5$)SO$_2$R$^6$, —NR$^5$CONR$^5$R$^6$, —C$_3$-C$_6$ cycloalkyl as defined above, 3–6 membered cycloheteroalkyl as defined above, aryl or heteroaryl as defined above, —SO$_2$NHCOR$^5$ or —CONHSO$_2$R$^5$ where R$^5$ is not hydrogen, —PO(OR$^5$)OR$^6$, —PO(OR$^6$)R$^5$, -tetrazol-5-yl, —C(O)NR$^5$OR$^6$, —NR$^5$C(=NR$^6$)NR$^5$R$^6$, —SO$_2$NHCONR$^5$R$^6$ or —SO$_2$NHCN;

with the proviso that when $R^1$ and $R^2$ are on adjacent carbons of A, $R^1$ and $R^2$ together with the carbons to which they are attached can form a 5–7 membered saturated or unsaturated monocyclic heterocyclic ring, or a 5–6 membered heteroaryl ring, each having from 1 to 2 heteroatoms independently selected from N, O, and S, wherein said heterocyclic or heteroaryl ring may be optionally substituted by one to four groups each selected independently from $R^4$; or $R^1$ and $R^2$ together with the carbons to which they are attached can form a 5–7 membered saturated or unsaturated carbocyclic ring or an aryl ring wherein said carbocyclic or aryl ring may be optionally substituted by one to four groups each selected independently from $R^4$;

R$^5$ and R$^6$ are independently defined as H, aryl and heteroaryl as defined above, —C$_3$-C$_6$-cycloalkyl as defined above, —C$_3$-C$_6$-cycloheteroalkyl as defined above, —C$_1$-C$_4$-perfluoroalkyl, or straight chain or branched —C$_1$-C$_6$ alkyl, —C$_2$-C$_6$-alkenyl, or —C$_2$-C$_6$-alkynyl each optionally substituted with —OH, —COR$^8$, —CN, —C(O)NR$^8$OR$^9$, —C$_2$-C$_6$-alkenyl, —C$_2$-C$_6$-alkynyl, —OR$^8$, —C$_1$-C$_4$-perfluoroalkyl, —S(O)$_x$R$^8$ where x is 0–2, —OPO(OR$^8$)OR$^9$, —PO(OR$^8$)R$^9$, —OC(O)NR$^8$R$^9$, —COOR$^8$, —CONR$^8$R$^9$, —SO$_3$H, —NR$^8$R$^9$, —NCOR$^8$R$^9$, —NR$^8$COOR$^9$, —SO$_2$NR$^8$R$^9$, —NO$_2$, —N(R$^8$)SO$_2$R$^9$, —NR$^8$CONR$^8$R$^9$, —C$_3$-C$_6$ cycloalkyl as defined above, —C$_3$-C$_6$-cycloheteroalkyl as defined above, -aryl or heteroaryl as defined above, —SO$_2$NHCOR$^8$ or —CONHSO$_2$R$^8$ where R$^8$ is not hyrdogen, -tetrazol-5-yl, —NR$^8$C(=NR$^9$)NR$^8$R$^9$, —SO$_2$NHCONR$^8$R$^9$, —SO$_2$NHCN;

R$^7$ is hydrogen, straight chain or branched —C$_1$-C$_6$-alkyl, —C$_2$-C$_6$-alkenyl, or —C$_2$-C$_6$-alkynyl each optionally substituted with —OH, —COR$^5$, —CN, —C$_2$-C$_6$-alkenyl, —C$_2$-C$_6$-alkynyl, —OR$^5$, —C$_1$-C$_4$-perfluoroalkyl, —S(O)$_x$R$^5$ where x is 0–2, —OPO(OR$^5$)OR$^6$, —PO(OR$^5$)R$^6$, —OC(O)NR$^5$R$^6$, —COOR$^5$, —CONR$^5$R$^6$, —SO$_3$H, —NR$^5$R$^6$, —NR$^5$COR$^6$, —NR$^5$COOR$^6$, SO$_2$NR$^5$R$^6$, —NO$_2$, —N(R$^5$)SO$_2$R$^6$, —NR$^5$CONR$^5$R$^6$, —C$_3$-C$_6$ cycloalkyl as defined above, —C$_3$-C$_6$-cycloheteroalkyl as defined above, -aryl or heteroaryl as defined above, —SO$_2$NHCOR$^5$ or —CONHSO$_2$R$^5$ where R$^5$ is not hydrogen, -tetrazol-5-yl, —NR$^5$C(=NR6)NR$^5$R$^6$, —C(O)N R$^5$OR$^6$, —SO$_2$NHCONR$^5$R$^6$ or —SO$_2$NHCN;

or R$^7$ is phenyl or naphthyl, optionally substituted by $R^1$, $R^2$, $R^3$ and $R^4$ or a 5 to 6 membered heteroaryl group having 1 to 3 heteroatoms selected independently from N, O, and S and optionally substituted by $R^1$, $R^2$, $R^3$ and $R^4$;

or R$^7$ is C$_3$-C$_6$ cycloalkyl or 3–6 membered cycloheteroalkyl as defined above;

or R$^7$CH$_2$—N—A—, where A is as defined above, can form with the carbon adjacent to the carbon bearing the sulfonamido group, a non-aromatic fused 7–10 membered heterocyclic ring optionally containing an additional heteroatomselected from O, S and N wherein said heterocyclic ring may be optionally fused to another benzene ring;

R$^8$ and R$^9$ are independently H, aryl or heteroaryl as defined above, —C$_3$-C$_7$-cycloalkyl or cycloheteroalkyl as defined above, —C$_1$-C$_4$-perfluoroalkyl, straight chain or branched —C$_1$-C$_6$-alkyl, —C$_2$-C$_6$-alkenyl, or —C$_2$-C$_6$-alkynyl, each optionally substituted with hydroxy, alkoxy, aryloxy, —C$_1$-C$_4$-perfluoroalkyl, amino, mono- and di-C$_1$-C$_6$-alkylamino, carboxylic acid, carboalkoxy and carboaryloxy, nitro, cyano, carboxamido primary, mono- and di-C$_1$-C$_6$-alkylcarbamoyl;

an optical isomer or diastereomer thereof;

or a pharmaceutically acceptable salt thereof.

2. A compound according to claim 1 wherein the Z group is para-alkoxyphenyl, para-aryloxyphenyl or para-heteroaryloxyphenyl.

3. A compound according to claim 2 which is selected from the group consisting of:

(trans)-2-[Benzyl-(4-methoxy-benzenesulfonyl)-amino]-cyclohexanecarboxylic acid hydroxyamide, and (cis)-2-[Benzyl-(4-methoxy-benzenesulfonyl)-amino]-cyclohexanecarboxylic acid hydroxyamide.

4. A method of inhibiting pathological changes mediated by matrix metalloproteinases in mammals which comprises administration to a mammal in need thereof a therapeutically effective amount of a matrix metalloproteinase inhibiting compound according to claim 1.

5. A method according to claim 4 wherein the condition treated is atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, infammatory bowel disease, or periodontal disease.

6. A method according to claim 4 wherein the condition treated is age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

7. A method of inhibiting pathological changes mediated by TNF-α converting enzyme (TACE) in mammals which comprises administration to a mammal in need thereof a therapeutically effective amount of a TACE inhibiting compound according to claim 1.

8. The method according to claim 7 wherein the condition treated is rheumatoid arthritis, graft rejection, cachexia, anorexia, inflammation, fever, insulin resistance, septic shock, congestive heart failure, inflammatory disease of the central nervous system, inflammatory bowel disease, or HIV infection.

9. A pharmaceutical composition comprising a pharmaceutical carrier and a therapeutically effective amount of a matrix metalloproteinase or TACE inhibiting compound according to claim 1.

* * * * *